United States Patent [19]
Pissiotas et al.

[11] 4,209,319
[45] Jun. 24, 1980

[54] HERBICIDALLY ACTIVE PHENYLFORMAMIDINE COMPOUNDS

[75] Inventors: Georg Pissiotas, Lörrach, Fed. Rep. of Germany; Dieter Duerr, Bottmingen; Otto Rohr, Therwill, both of Switzerland

[73] Assignee: Ciba-Geigy Corporation, Ardsley, N.Y.

[21] Appl. No.: 692,066

[22] Filed: Jun. 2, 1976

Related U.S. Application Data

[63] Continuation-in-part of Ser. No. 311,057, Dec. 1, 1972, abandoned.

[51] Int. Cl.$^2$ .................. C07C 123/00; A01N 9/20
[52] U.S. Cl. .................. 71/121; 260/501.14; 260/564 RF
[58] Field of Search ....... 260/564 RF, 456 A, 501.14; 424/326, 316, 303; 71/121, 86, 103, 113, 115

[56] References Cited
U.S. PATENT DOCUMENTS
3,857,836  12/1974  Horlein et al. ................ 260/564 RF FOREIGN PATENT DOCUMENTS
792407  12/1972  Belgium .................. 260/564 RF Primary Examiner—Bernard Helfin
Assistant Examiner—L. Hendriksen
Attorney, Agent, or Firm—Frederick H. Rabin

[57] ABSTRACT

New phenylformamidine compounds are disclosed, which have the structure

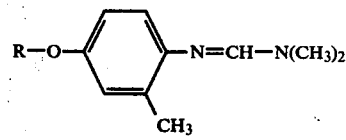

in which R is an unsaturated, halogenated radical, particularly a propenyl, butenyl or benzyl radical, mono- or disubstituted by fluorine chlorine or bromine. These compounds and their acid addition salts possess herbicidal properties.

12 Claims, No Drawings

HERBICIDALLY ACTIVE PHENYLFORMAMIDINE COMPOUNDS

CROSS-REFERENCE TO RELATED APPLICATION

This application is a continuation-in-part of our application, Ser. No. 311,057 filed Dec. 1, 1972, now abandoned.

The present invention relates to new phenylformamidines, process for their manufacture, their use in regulating plant growth, as well as to herbicidal compositions which contain these compounds as active substances together with carriers.

The phenylformamidine compounds of the present invention correspond to the formula I

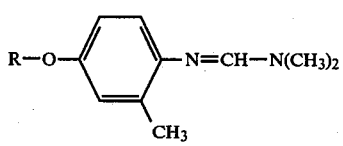

in which R is an unsaturated halogenated radical, particularly a propenyl, butenyl or benzyl radical, that is mono- or di-substituted by fluorine, chlorine or bromine, and their acid addition salts with inorganic and organic acids.

Preferred are those compounds, which are substituted by chlorine.

Possible addition salts have to be agriculturally acceptable and include those of moderately strong or strong inorganic or organic acids. Examples of such acids are: hydrochloric acid, hydrobromic acid, phosphoric acid, sulphuric acid, fluoroboric acid (HBF$_y$), per-chloric acid, methyl- or ethysulphuric acid, methyl- or ethylsuphonic acid, benzene sulphonic acid, p-toluenesulphonic acid, acetic acid, monochloroacetic acid, dichloroacetic acid, trichloroacetic acid, α-chloropropionic acid, oxalic acid, maleic acid, tartaric acid, and dichlorobenzoic acid.

Preferred are the acid addition salts in which the acid is hydrochloric, sulfuric or p-toluenesulfonic.

The compounds of the formula I can be manufactured by methods which are known in the art and illustrated by the following reaction schemes:

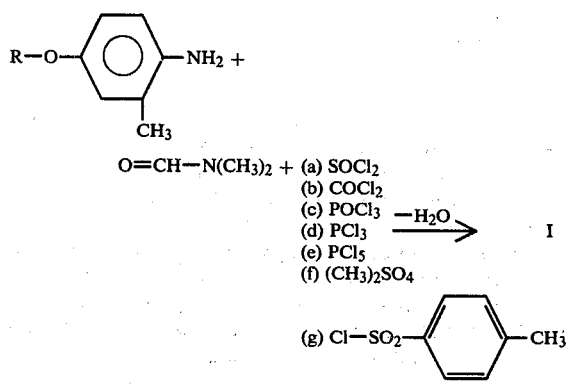

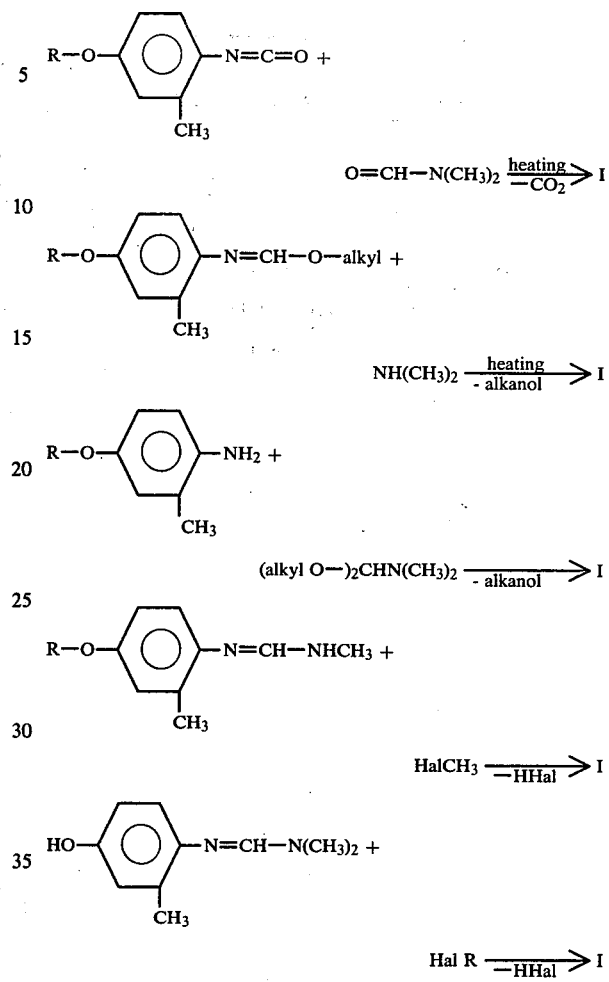

In the above formulae, R has the meanings given under formula I, alkyl stands for $C_1$–$C_4$ alkyl, preferably methyl or ethyl, alkanol for a $C_1$–$C_4$ alkanol preferably methanol or ethanol and Hal represents chlorine or bromine.

The following example illustrates the manufacture of the new formamidine compounds of this invention. In the following table are listed further compounds which are obtained in an analogous manner. Temperatures are given in degrees centigrade.

EXAMPLE 1

N-[2-methyl-4-(β-chloralllyloxy)-phenyl]-N',N'-dimethylformamidine

While stirring, 30.5 ml of 2,3-dichloropropene are added dropwise at 10°–15° to a mixture of 53.5 g of N-(2-methyl-4-hydroxyphenyl)-N'-N'-dimethylformamidine, 20 g of pulverised potassium hydroxide and 300 ml of dry dimethylsulphoxide. Stirring of the mixture is continued for 12 hours at room temperature. It is then poured on ice water and extracted with benzene. The benzene solution is dried over sodium sulphate, evaporated, and the residue distilled in vacuo to give the above compound with a boiling point of 125°–130°/0.02 Torr.

| No. | R | physical property | salt |
|---|---|---|---|
| 1 | CH$_2$=CCl—CH$_2$— | b.p. 125–130°/0.02 | HCl m.p. 135–136° |
| 2 | ClCH=CH—CH$_2$— | n$_D^{25}$ 1.5781 | |
| 3 | ClCH=CCl—CH$_2$— | | |
| 4 | CH$_2$=CBr—CH$_2$— | n$_D^{23}$ 1.5912 | |
| 5 | CH$_3$—CCl=CH—CH$_2$— | n$_D^{25}$ 1.5750 | |
| 6 | (3-Cl-benzyl) | n$_D^{25}$ 1.6049 | HCl m-p-199–200° |
| 7 | (2-Cl-benzyl) | m.p. 67–67.5° | |
| 8 | (benzyl) | n$_D^{23}$ | |
| 9 | (2-Cl-4-CH$_3$-benzyl) | m.p. 49–50° | |
| 10 | (2,4-diCl-benzyl) | m.p. 70–71° | |
| 11 | (2,6-diCl-benzyl) | m.p. 84–85° | |
| 12 | (3-F-benzyl) | n$_D^{23}$ 1.5907 | |
| 13 | (2,4-diF-benzyl) | m.p. 62–64° | |
| 14 | (3-Br-benzyl) | m.p. 72–73° | |

The compounds of this invention are new. Phenylformamidines of similar structure are known from U.S. Pat. No. 3,284,289, which possess mainly insecicidal activity and from U.S. Pat. No. 3,857,836 which possess herbicidal activity. The compounds of the present invention are structurally distinct and possess herbicidal properties and are suitable for controlling grass-like and latifoliate weeds in various crop plant cultures. When used in high concentrations the new compounds act as total herbicides; on the other hand, when used in lower concentrations they act as selective herbicides. Deep rooted, difficulty combattable weeds which are one or more years old are successfully damaged in their growth or destroyed by the active substances of the formula I. The new active substances can be applied with the same good success before germination (pre-emergence) and after germination (postermergence). Thus meadow weeds, for example millet species (Panicum spp.), mustard species (Chenopodiaceae), slender foxtail (Alopecurus spp.) and other foxtail species, e.g. Amaranthus spp., grasses, e.g. Lolium spp., Compositae, e.g. Taraxacum spp., camomile species (Matricaria spp.), are destroyed or hindered in their growth without damage being caused to cultivated plants, such as cereals, maize, cotton, and sorghum. The rates of application vary and are dependent on the time of application; they are between 0.1 to 10 kg of active substance per hectare. In order to totally destroy entire crops of weeds, for example on fallow land neighbouring on the cultivated areas, it is necessary to use more than 10 kg per hectare. The usual crop rotation may proceed on application of the new active substances without any detrimental effects.

The new compounds may be used in combination with herbicides of other chemical classes of substance, to effect an improvement in activity.

The compounds of the formula I may be used as pure active substance or together with suitable carriers and/or additives. Suitable carriers and additives can be solid or liquid and correspond to the substances conventionally used in formulation technique such, for example, as solvents dispersants, wetting agents, adhesives, thickeners, binders and/or fertilisers.

For application, the compounds of the formula I may be processed to dusts, emulsion concentrates, granules, dispersions, sprays, to solutions, or suspensions in the conventional formulation which is commonly employed in application technology.

The compositions according to the invention are manufactured in known manner by intimately mixing and/or grinding active substances of the formula I with the suitable carriers, optionally with the addition of dispersants or solvents which are inert towards the active substances. The active substances may take and be used in the following forms:

Solid forms:
Dusts, tracking agents, granules, coated granules, impregnated granules and homogeneous granules.

Liquid forms:
(a) active substances which are dispersible in water: wettable powders, pastes, emulsions;
(b) solutions.

To manufacture solid forms (dusts, tracking agents), the active substance are mixed with solid carriers. Suitable carriers are, for example: kailin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substance can either be used alone or in admixture with one another.

Granules can be very easily manufactured by dissolving an active substance of the formula I in an organic solvent an applying the resulting solution to a granulated material, for example attapulgite, $SiO_2$, granicalcium, bentonite etc. and then evaporating the solvent.

Polymer granules can also be manufactured by mixing the active substances of the formula I with polymerisable compound (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvdent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixture can also be added additives which stabilize the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivates (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleyol ethionate, the sodium salt of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove in such a manner that, in wettable powders, the solid particle size of from 0.02 to 0.04$\mu$ and in pastes, of 0.03$\mu$ is not exceeded. To procedure emulsifiable concentrates and pastes, dispersing agents such as those cited above, organic solvents and water are used. Examples of suitable solvents are: alcohols, benzene, xylene, toluene, dimethyl sulfoxide, and mineral oil fractions boiling between 120° and 350° C. The solvents must be practically odourless, not phytotoxic, inert to the active substances.

Furthermore, the agents according to the invention can be applied in the form of solutions. For this purpose the active substance or several active substances of the general formula I are dissolved in suitable organic solvents, mixtures of solvents or in water. Aliphatic and aromatic hydrocarbons, chlorinated derivatives thereof, alkyl naphthalenes, and mineral oils singly or in admixture with each other, can be used as organic solvents.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 22% dust:

(a)

5 parts of active substance
95 parts of talcum (b)

2 parts of active substance
1 part of highly disperse silica
97 parts of talcum.

The active substance are mixed with the carriers and ground.

Granules

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder:

The following constituents are used for the preparation of (a) a 40%, (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silica acid.

(b)

25 parts of active substance,
4.5 parts of calcium lignin sulfphonate
1.9 parts of Champagne chalk/hydroxyethyl cellulose mixture (1:1),
1.5 parts of sodium dibutyl naphthalene sulphonate,
19.5 parts of silica acid,
19.5 parts of Champagne chalk,
28.1 parts of kaolin.

(c)

25 parts of active substance,
2.5 parts of isooctylphenoxy-poloxyethylene-ethanol,
1.7 parts of Champagne chalk/hydroxyethyl cellulose mixture (1:1),
8.3 parts of sodium aluminium silicate,
16.5 pats of kieselguhr,
46 parts of kaolin,
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then groun in the appropriate mills and rollers. Wettable powder are obtained which can be diluted with water to give suspensions of any desired concentration.

Emulsifiable concentrates:

The following substances are used to produce (a) a 10% and (b) a 25% emulsifiable concentrate:

(a)

10 parts of active substance,
3.4 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene,
25 parts of active substance,
2.5 parts of epoxidised vegetable oil,
10 parts of an alkylarylsulphonate/fatty alcohol-polyglycol ether mixture,
5 parts of dimethylformamide,
57.5 parts of xylene.

From these concentrates it is possible to produce, by dilution with water, emulsions of any desired concentration.

Spray:

The following constituents are used to prepare a 5% spray:

5 parts of active substance,
1 part of epichlorohydrin,
94 parts of benzene (boiling limits 160°–190° C.).

EXAMPLE 2

Herbicidal action on preemergence application

The active substance in the form of a 10% powder concentrate is worked into earthenware pots filled with garden soil in a concentration equivalent to 2,1 and 0.5 kg of active substance per hectare. Crop plants and weeds are sown in the thus prepared soil.

The pots are then kept under daylight in a greenhouse at 22°–25° C. and 50% to 70% relative humidity. Evaluation of the tests takes place after 20 days. The result is given in the following Table.

Composition of the powder concentrate:

10 parts of active substance, 0.6 part of sodium dibutylnaphthalenesulphonate, 1 part of naphthalenesulphonic acid/phenolsulphonic acid/formaldehyde condensate (3:2:1), 10 parts of sodium aluminium silicate, 78.4 parts of kaolin.

Rating

The state of the plants was rated according to the following scale.
9 = plants undamaged
1 = plants destroyed
8–2 = intermediate stages of damage
— = not tested

| Compound No. | kg active substance/ha | oats | wheat | maize | sorghum | rice | soya | cotton | sugar beet | Galium | Chrysanthemum | Amaranthus | Echinochloa | Setaria | Digitaria | Alopecurus | Lolium |
|---|---|---|---|---|---|---|---|---|---|---|---|---|---|---|---|---|---|
| 1 | 2 | 7 | 7 | — | 7 | 9 | — | 7 | — | 2 | 1 | 1 | 1 | 1 | 1 | 2 | — |
|  | 1 | 8 | 8 | — | 7 | 9 | 8 | 8 | — | 2 | 2 | 1 | 1 | 2 | 1 | 3 | — |
|  | 0.5 | 9 | 9 | — | 9 | 9 | 9 | 9 | — | 2 | 3 | 1 | 1 | 3 | 2 | 3 | — |
| 1 HCl salt | 2 | — | 6 | — | — | — | 7 | 9 | 8 | 2 | — | 1 | 1 | 1 | 1 | 1 | 1 |
|  | 1 | — | 7 | — | — | — | 8 | 9 | 9 | 3 | — | 1 | 1 | 1 | 1 | 1 | 2 |
|  | 0.5 | — | 8 | — | — | — | 9 | 9 | 9 | 3 | — | 1 | 2 | 3 | 2 | 3 | 3 |
| 6 | 2 | — | — | — | — | — | 8 | 9 | — | 2 | 1 | 1 | — | 1 | 1 | 2 | 1 |
|  | 1 | — | — | — | — | — | 9 | 9 | — | 2 | 1 | 1 | — | 1 | 1 | 2 | 1 |
|  | 0.5 | — | — | — | — | — | 9 | 9 | — | 3 | 2 | 1 | — | 1 | 1 | 3 | 2 |
| 6 HCl salt | 2 | — | 7 | 7 | 9 | — | 7 | 9 | 8 | 2 | 1 | 1 | 1 | 2 | 1 | — | — |
|  | 1 | — | 8 | 7 | 9 | — | 8 | 9 | 9 | 3 | 1 | 1 | 1 | 2 | 1 | — | — |
|  | 0.5 | — | 9 | 8 | 9 | — | 9 | 9 | 9 | 3 | 4 | 1 | 1 | 4 | 1 | — | — |
| 2 | 2 | 7 | 7 | — | — | 8 | 7 | 9 | 7 | — | 2 | 1 | 2 | — | 1 | 2 | — |

-continued

| Compound No. | kg active substance/ha | oats | wheat | maize | sorghum | rice | soya | cotton | sugar beet | Galium | Chrysanthemum | Amaranthus | Echinochloa | Setaria | Digitaria | Alopecurus | Lolium |
|---|---|---|---|---|---|---|---|---|---|---|---|---|---|---|---|---|---|
| | 1 | 7 | 8 | — | — | 8 | 8 | 9 | 8 | — | 2 | 1 | 3 | — | 2 | 2 | — |
| | 0.5 | 8 | 8 | — | — | 9 | 9 | 9 | 9 | — | 2 | 1 | 3 | — | 3 | 3 | — |

EXAMPLE 3

The plants were sown into earthenware pots filled with sterile earth and watered. The following day the pots were sprayed with a suspension of the test compound so that an amount corresponding respectively to 16 and 4 kg per hectare of active substance was applied. The pots are then kept for 20 days in the green house under the same conditions as in the above test and the state of the plants was then evaluated.

A. The results are given in the following Table. Three compounds known from U.S. Pat. No. 3,857,836 were also tested:

A. N-(para-1,2-dichlorovinyloxy-phenyl)-N',N'-dimethylformamidine

B. N-(meta-1,2-dichlorovinyloxy-phenyl)-N',N'-dimethylformamidine

C. N-(para-1,2-dichlorovinyloxy-meta-methylphenyl)-N',N'-dimethylformamidine

| plant | application rate in kg/ha | 1 | compound 1 HCl salt | 2 3 6 A B C |
|---|---|---|---|---|
| avena fatua | 16 | 4 | 2 | 7 4 6 9 8 9 |
| sinapis alba | 16 | 1 | 1 | 3 3 1 9 6 7 |
| sinapis alba | 4 | 3 | 3 | 2 6 2 9 8 9 |
| setaria italica | 4 | 1 | 1 | 1 1 1 9 8 9 |

We claim:

1. A phenylformamidine compound of formula I

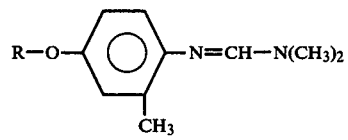

wherein R is propenyl mono- or disubstituted by chlorine or bromine and its acid plant growth regulating acceptable addition salts.

2. A compound according to claim 1 wherein R is propenyl mono- or disubstituted by chlorine.

3. An acid addition salt according to claim 1 with in which the acid is hydrochloric, sulfuric or p-toluene sulfonic.

4. The compound of claim 1, which is N-[2-methyl-4-(β-chlorallyloxy)-phenyl]-N'N'-dimethylformamidine.

5. The compound of claim 1, which is N-[2-methyl-4-(β-chlorallyloxy)-phenyl]-N'N'-dimethylformamidine hydrochloride.

6. The compound of claim 1, which is N-[2-methyl-4-(β,γ-dichlorallyloxy)-phenyl]-N'N'-dimethylformamidine.

7. The compound N-[2-methyl-4-(γ-chlorbut-2-enyloxy)-phenyl]-N'N'-dimethylformamidine.

8. A herbicidal composition containing as active ingredient a herbicidally effective amount of a phenylformamidine compound of formula I claim 1 or an acid addition salt thereof according to claim 1 together with an inert carrier and/or extender.

9. A method of controlling undesirable plant growth which comprises applying to a locus where undesirable plant growth is to be controlled, a herbicidally effective amount of a phenylformamidine compound of formula I or an acid addition salt thereof according to claim 1.

10. A method according to claim 9 which consists in selectively controlling weeds in cultures of crop plants.

11. A method according to claim 10 which consists in selectively controlling weeds in cultures of grain crops or cotton.

12. The method of claim 10 when used in pre-emergence application.

* * * * *